United States Patent [19]

Pellico

[11] 4,381,947

[45] May 3, 1983

[54] SETTABLE ALGINATE COMPOSITIONS

[75] Inventor: Michael A. Pellico, Los Angeles, Calif.

[73] Assignee: Laclede Professional Products, Inc., Brooklyn, N.Y.

[21] Appl. No.: 378,917

[22] Filed: May 17, 1982

Related U.S. Application Data

[63] Continuation-in-part of Ser. No. 220,303, Dec. 29, 1980, abandoned.

[51] Int. Cl.³ ............................................. C08L 5/04
[52] U.S. Cl. .................................. 106/38.5 D; 106/35; 106/206; 106/208; 106/209; 433/213; 433/214
[58] Field of Search .................. 106/38.5 D, 209, 206, 106/208, 35; 433/213, 214

[56] References Cited

U.S. PATENT DOCUMENTS

| | | | |
|---|---|---|---|
| 2,298,835 | 10/1942 | Noyes | 106/38.5 D |
| 2,657,971 | 11/1953 | Lochridge | 106/38.5 D |
| 2,756,874 | 7/1956 | Erickson et al. | 106/38.5 D |
| 2,816,843 | 12/1957 | Erickson | 106/38.5 D |
| 3,268,348 | 8/1966 | Morrell | 106/38.5 D |

*Primary Examiner*—Lorenzo B. Hayes

[57] ABSTRACT

An oral, settable, dental composition is prepared by interacting Component A containing an alkali metal alginate in an aqueous paste with Component B containing a divalent metal salt such as calcium sulfate and a reaction rate retarder such as tetrasodium pyrophosphate in a fluid plasticizer paste that is substantially free of unbound water.

24 Claims, No Drawings

SETTABLE ALGINATE COMPOSITIONS

CROSS-REFERENCE TO RELATED APPLICATION

This application is a continuation-in-part of U.S. patent application Ser. No. 220,303, filed Dec. 29, 1980, now abandoned, for Settable Alginate Compositions.

BACKGROUND OF THE INVENTION

This invention relates to self-contained, two-component, interactable and orally settable alginate systems which are particularly adapted for use in dental therapeutics.

Alginate compositions have long been used in dentistry as impression materials for making impressions in areas in which partial dentures are to be constructed, for fabricating study models in orthodontic treatment, for making primary impressions in endentulous mouths, and as corrective materials in secondary impressions of all types.

As distinguished from agar-based thermally reversible hydrocolloids which gel by lowering the temperature of the heated and fluidized material, alginate compositions gel by means of a chemical reaction. After the alginate gel is formed, it cannot be converted to a fluid condition or sol by physical means and, thus, the alginates are known as irreversible hydrocolloids. The use of alginates in dental therapeutics is reviewed in the text entitled *Elements of Dental Materials,* by Ralph Phillips at Chapter 9.

Alginate compositions designed for use in dental therapeutics are typically formulated as powders which are adapted to be mixed with water to form a viscous sol. The sol is carried into the mouth in a perforated impression tray where it forms an elastic gel through a series of chemical reactions. Following formation of the gel, the impression is removed from the mouth for use in the construction of dental forms.

The principal ingredients of a prior art, powdered alginate impression material are illustrated by the following formula: potassium alginate (12%), diatomaceous earth (74%), calcium sufate (dihydrate) (12%), and trisodium phosphate (2%). The significant ingredient in the formulation is soluble potassium alginate which is derived from sea kelp. When the powdered alginate formulation is mixed with water, the soluble alginate reacts with the calcium sulfate to produce the gel structure of an insoluble calcium alginate. Since this reaction must take place and go to completion in the mouth, it must be delayed until the aqueous composition is placed in the impression tray and carried to the mouth. In order to effect this delay and provide adequate working time, a reaction rate retarder such as trisodium phosphate is incorporated into the formulation. The suggested mechanism for the effectiveness of the reaction rate retarder is that the calcium sulfate will reach first with the trisodium phosphate before reacting with the soluble alginate and that as long as any trisodium phosphate is present, the gelling reaction between the soluble alginate and the calcium sulfate will be prevented. A filler such as diatomaceous earth is also incorporated into the formulation to increase the strength and stiffness of the gel and to provide a firm surface that is not tacky. The final structure of the gel is characterized as a brush-heap network of fibrils of calcium alginate which hold the excess water and filler.

The powdered alginate compositions of the prior art have certain inherent problems. One of the problems encountered is that the water used in preparing the gel contains dissolved minerals such as calcium and iron salts which alter the divalent metal concentration in the powder formulation. The presence of the additional divalent metal ions can cause a grainy mix and uneven gel formation and, in addition, can have an adverse effect on the control of set time. This type of problem is most severe in those regions where the water supply has a high mineral content; and this type of problem is also vexing in those regions where the mineral content of the water supply varies throughout the day.

A second problem encountered with the powdered alginate compositions of the prior art relates to the temperature of the water used in the preparation of the gel, since this temperature is a principal factor in determining gelation or set time. In general, gelation time of the alginate composition is inversely proportional to the temperature of the admixing water. Accordingly, by increasing the water temperature, the gelation time is reduced. Likewise, if fluidity or flow of the material is measured against the temperature of the mixing water, the same relationship occurs, namely, the duration of the flow is inversely proportional to the temperature of the water. Flow is an important characteristic of the material, since the impression material must be fluid enough to move into intimate contact with the tissue so as to provide an accurate impression. Alginate formulations are usually designed to set in 2-3 minutes when mixed with water having a temperature of 72° F. However, the temperature of the supply water varies from day to day and during the day in many regions which makes flow characteristics and set time difficult to control.

Also, the stone die must be added promptly to the alginate impression of the prior art so as to minimize inaccuracy through impression shrinkage as a result of water evaporation.

In addition, shelf life has been a continuing problem with powdered alginate formulations which deteriorate rapidly at elevated temperatures, or in the presence of moisture, or under both conditions resulting in the aqueous alginate formulation either failing to set at all or setting much too rapidly. This type of problem is accentuated by the association of a small amount of water with the ingredients used in making up the formulation.

Accordingly, it would be advantageous to provide an alginate system where the alginate is separated from the divalent metal ions until the time of use, where the system is self-contained with respect to water and thereby avoids the problem associated with varying water temperature and dissolved minerals, and where the system is formulated with humectants and plasticizers for enhanced stability and impression accuracy.

SUMMARY OF THE INVENTION

In accordance with one aspect of this invention, there is provided a two-component system interactable to form an oral, settable, dental composition comprising:

(i) Component A containing an alkali metal alginate selected from the group consisting of sodium alginate, potassium alginate and mixtures thereof in an aqueous paste; and (ii) Component B containing a slightly water soluble divalent metal salt and a reaction rate retarder in a fluid plasticizer paste, said Component B being so formulated that a pre-selected quantity thereof contains from about 0.5 to about 1.2 parts by weight of divalent metal salt per 1.0 part by weight of alkali metal alginate in Component A, said reaction rate retarder being present in an amount from about 0.02 to about 0.13 part by weight per 1.0 part by weight of said divalent metal salt, and said fluid plasticizer being present in an amount from about 0.75 to about 2 parts by weight per 1.0 part by weight of said divalent metal salt.

In accordance with a second aspect of this invention, there is provided a method for preparing an oral, settable, dental composition which comprises interacting Components A and B having formulations as hereinabove described.

In a third aspect of this invention, there is provided a solid, coherent, dental composition prepared by interacting Components A and B having formulations as hereinabove set forth.

DETAILED DESCRIPTION

The alkali metal alginates which are utilized in this invention include sodium alginate, potassium alginate and mixtures thereof. In contrast to the powdered alginate formulations of the prior art which called for the use of low calcium and relatively low molecular weight alkali metal alginates in order to facilitate in use solubilization of the same, this invention permits the use of relatively high calcium and high molecular weight alkali metal alginates through pre-solubilization as hereinafter described to thereby provide an alginate impression material having a higher gel strength. The alkali metal alginates, which are derived from sea kelp, generally have a molecular weight from about 32,000 to about 250,000. The alginic acid moiety is characterized as a polysaccharide composed of beta-D-mannuronic acid residues linked so that the carboxyl group of each unit is free, while the aldehyde group is shielded by a glycosidic linkage. It is further characterized as a linear polymer of the mannuronic acid in the pyranose ring form.

The divalent metal salt which is interacted with the alkali metal alginate to provide a settable dental composition is, advantageously, a slightly water soluble, nontoxic divalent metal salt such as calcium sulfate, ferrous sulfate, zinc sulfate, as well as divalent metal salt of fatty acid such as calcium oleate, zinc laurate, ferrous stearate, and mixtures thereof. A particularly effective divalent metal salt is calcium sulfate dihydrate which is known commercially as terra alba.

The divalent metal salt is generally employed in an amount from about 0.5 to 1.2 parts by weight per 1.0 part by weight of alkali metal alginate and, preferably, in an amount from about 0.75 to about 1.0 part by weight per 1.0 part by weight of alkali metal alginate.

The reaction rate retarders which can be utilized in this invention are incorporated in the divalent metal salt component of the two-component system and may, advantageously, also be included in the alkali metal alginate component of this system in order to moderate the rate of reaction between the divalent metal salt and the alkali metal alginate and thereby provide suitable working and set time for the impression material. The reaction rate retarder includes, for example, trisodium and tripotassium phosphates, tetrasodium and tetrapotassium pyrophosphates, trisodium and tripotassium citrates, and trisodium and tripotassium silicates as well as mixtures thereof.

The reaction rate retarder is generally present in the divalent metal salt component in an amount from about 0.02 to about 0.13 part by weight per 1.0 part by weight of the divalent metal salt, and, preferably, in an amount from about 0.04 to about 0.08 part by weight per 1.0 part by weight of the divalent metal salt. The reaction rate retarder may also, with advantage, be included in the alkali metal alginate component in an amount from about 0.02 to about 0.08 part by weight per 1.0 part by weight of alkali metal alginate.

Fluid plasticizers which can be used as the non-aqueous carrier or vehicle for the divalent metal salt component include monhydric alcohol, polyhydric alcohol, vegetable oil, light mineral oil, light silicone oil and mixtures thereof. Illustrative mono- and polyhydric alcohols include oleyl alcohol, propylene glycol, polyether glycols and glycerol. Illustrative vegetable oils include almond oil, peanut oil, olive oil, safflower oil, soybean oil and the like. Vegetable oils are advantageous because they have a low affinity for water. The fluid plasticizer is generally present in an amount from about 0.75 to about 2 parts by weight per 1.0 by weight of the divalent metal salt and, preferably, in an amount from about 0.9 to about 1.5 parts by weight per 1.0 part by weight of the divalent metal salt. Suitable mixtures of the fluid plasticizers include: (a) glycerol and light silicone oil, (b) glycerol and light mineral oil, and (c) vegetable oil exemplified by almond oil (sweet) and polyether glycol exemplified by The Dow Chemical Company polyglycol 15-200 (an oxyethylene/oxypropylene condensate of glycerol).

The divalent metal salt component of this invention should be substantially free of unbound water. The term unbound water refers to free water and, as such, is distinguishable from bound water which is present in, for example, calcium sulfate dihydrate. While the divalent metal salt component may satisfactorily tolerate the presence of a relatively small amount of water as, for example, an amount up to about 1.0 wt. %, the presence of any significant amount of free water such as an amount approximating or in excess of 5.0 wt. % will result in impairment of product utility through storage deterioration in that this component will set up and harden during storage. Thus, to assure product utility, it is essential and necessary to restrict the amount of any free water in the divalent metal salt component to less than 5.0 wt. %, preferably, less than 3.0 wt. % and, optimally, less than 1.0 wt. %.

Gel strength of the alginate impression can be enhanced by incorporating into the divalent metal salt component a metal oxide such as zinc oxide, magnesium oxide or mixtures thereof generally in an amount from about 0.02 to about 1.0 part by weight per 1.0 part by weight of divalent metal salt and, preferably, in an amount from about 0.08 to about 0.6 part by weight per 1.0 part by weight of divalent metal salt. Previous attempts to incorporate metal oxide in powdered alginate formulations tended to be unsuccessful because when water was added to the powder, the metal oxide affected the solubility of the sodium alginate and it was difficult to mix the powder smoothly into the aqueous medium and, in addition, the aqueous composition had a tendency to be grainy.

A filler is advantageously included in the alkali metal alginate component. Examples of fillers which can be used include diatomaceous earth, silica, talc and mixtures thereof. A perferred filler is diatomaceous earth. The filler is generally present in an amount from about 3 to about 10 parts by weight per 1.0 part by weight of alkali metal alginate and, preferably, in an amount from about 5 to about 8 parts by weight per 1.0 par by weight of alkali metal alginate.

Water is included in the alkali metal alginate component in order to provide an aqueous fluid vehicle for this component and to provide an aqueous environment for the interaction of the alkali metal alginate with the divalent metal salt to form the insoluble alginate. Water is generally present in an amount from about 13 to about 25 parts by weight per 1.0 part by weight of alkali metal alginate and, preferably, in an amount from about 15 to about 21 parts by weight per 1.0 part by weight of alkali metal alginate.

A reaction rate retarder as, for example, a member selected from the group consisting of phosphate, pyrophosphate, citrate and silicate salts of sodium, potassium and mixtures thereof may advantageously be included in the alkali metal alginate component. The reaction rate retarder, in this component, is generally present in an amount from about 0.02 to about 0.08 part by weight per 1.0 per by weight of alkali metal alginate and, preferably, in an amount from about 0.03 to about 0.06 part by weight per 1.0 part by weight of alkali metal alginate.

The alkali metal alginate component is advantageously formulated with a humectant to effect moisture control and thereby enhance impression accuracy. Illustrative humectants which can be used include glycols such as propylene glycol, polyether glycols and diethylene glycol, sugar alcohols such as sorbitol, sugars such as dextrose, light oils and mixtures thereof. The humectant is generally present in an amount from about 0.1 to about 1.0 part by weight per 1.0 part by weight of alkali metal alginate and, preferably, in an amount from about 0.15 to about 0.5 part by weight per 1.0 part by weight of alkali metal alginate.

The composition comprising the alkali metal alginate is hereinafter referred to as "Component A" while the composition comprising the divalent metal salt is hereinafter referred to as "Component B". Components A and B are so formulated with their dry and liquid constituents as to form light pastes which can be readily scooped or dispensed from suitable containers and easily and smoothly intermixed to form an orally, settable composition. In use, Components A and B are so formulated that specified quantities of these components provide from about 0.5 to about 1.2 parts by weight of divalent metal salt per 1.0 part by weight of alkali metal alginate. In a specific application, Components A and B are so formulated that 4 volumes of Component A and 1 volume of Component B provide quantities of alkali metal alginate and divalent metal salt within the aforesaid weight ratios.

EXAMPLES

The following examples further illustrate the invention.

In Example I through Example IV, Components A and B were prepared by blending the dry ingredients with the fluid ingredients in a high-speed, stainless steel blender to form light pastes. The formulations were so designed that 4 volumes of Component A and 1 volume of Component B provided suitable weight ratios for interacting the alkali metal alginate with the divalent metal salt. Components A and B were evaluated for pre-mix shelf life and ease of mixing, and resulting mixtures of Components A and B were evaluated for set time and moisture loss at 72° F. Components A and B were hand-mixed in a plastic mixing bowl. Set time was measured as the length of time to convert the fluid composition to a tack-free gel. Moisture loss was determined by weight difference over a specified period of time.

EXAMPLE I

| COMPONENT A | PARTS BY WT. | COMPONENT B | PARTS BY WT. |
| --- | --- | --- | --- |
| Sodium alginate | 11 | Magnesium oxide | 5 |
| Diatomaceous earth | 84 | Calcium sulfate | 45 |
| Potassium pyrophosphate | 1 | Potassium pyrophosphate | 4 |
| Dextrose | 2 | Glycerol | 35 |
| Diethylene glycol | 2 | Silicone oil | 5 |
| water | 150 | Diatomaceous earth | 6 |
| Preservative | Trace | | |
| Flavor | Trace | | |
| Pre-mix shelf life: | | Excellent | |
| Ease of mixing: | | Very easy | |
| Set time, minutes: | | 3 | |
| Moisture loss, 30 minutes: | | 0.4 wt. % | |

EXAMPLE II

| COMPONENT A | PARTS BY WT. | COMPONENT B | PARTS BY WT. |
| --- | --- | --- | --- |
| Sodium alginate | 11 | Magnesium oxide | 5 |
| Diatomaceous earth | 84 | Calcium sulfate | 45 |
| Potassium pyrophosphate | 1 | Potassium pyrophosphate | 4 |
| Diethylene glycol | 4 | Glycerol | 35 |
| Water | 150 | Silicone oil | 5 |
| Preservative | Trace | Diatomaceous earth | 6 |
| Flavor | Trace | | |
| Pre-mix shelf life: | | Excellent | |
| Ease of mixing: | | Very easy | |
| Set time, minutes: | | 3 | |
| Moisture loss, 30 minutes: | | 0.5 wt. % | |

EXAMPLE III

| COMPONENT A | PARTS BY WT. | COMPONENT B | PARTS BY WT. |
| --- | --- | --- | --- |
| Sodium alginate | 12 | Magnesium oxide | 5 |
| Diatomaceous earth | 86 | Calcium sulfate | 45 |
| Potassium pyrophosphate | 2 | Potassium pyrophosphate | 4 |
| Water | 150 | Glycerol | 35 |
| Preservative | Trace | Silicone oil | 5 |
| Flavor | Trace | Diatomaceous earth | 6 |
| Pre-mix shelf life: | | Excellent | |
| Ease of mixing: | | Very easy | |
| Set time, minutes: | | 3.5 | |
| Moisture loss, 30 minutes: | | 1.9 wt. % | |

EXAMPLE IV

| COMPONENT A | PARTS BY WT. | COMPONENT B | PARTS BY WT. |
| --- | --- | --- | --- |
| Potassium alginate | 11 | Calcium sulfate | 50 |
| Diatomaceous earth | 50 | Trisodium phosphate | 4 |
| Tetrasodium pyrophosphate | 0.5 | Glycerol | 60 |
| Sorbitol | 5 | Silica | 11 |
| Propylene glycol | 2 | | |
| Water | 150 | | |
| Flavor | 0.4 | | |
| Preservative | 0.2 | | |
| Pre-mix shelf life: | | Excellent | |
| Ease of mixing: | | Very easy (no agregation) | |

| COMPONENT A | PARTS BY WT. | COMPONENT B | PARTS BY WT. |
|---|---|---|---|
| Set time, minutes: | 3 | | |
| Moisture loss, 30 minutes: | 0.2 wt. % | | |

EXAMPLE V

This example illustrates a formulation for Component A which has a very heavy, putty-like consistency.

| COMPONENT A | PARTS BY WT. |
|---|---|
| Potassium alginate | 20 |
| Talc | 50 |
| Sodium polyphosphate | 3 |
| Sorbitol | 10 |
| Water | 120 |
| Flavor | Trace |
| Color | Trace |
| Preservative | Trace |

EXAMPLE VI

This example illustrates various ingredients and proportions thereof which can be used in formulating Component B.

| INGREDIENTS | WT. % |
|---|---|
| Example 6(a). | |
| Calcium sulfate | 50 |
| Potassium pyrophosphate | 2 |
| Propylene glycol | 38 |
| Zinc oxide | 10 |
| Example 6(b). | |
| Calcium sulfate | 30 |
| Sodium pyrophosphate | 2 |
| Diethylene glycol | 55 |
| Zinc oxide | 8 |
| Example 6(c). | |
| Zinc sulfate | 30 |
| Tetrasodium pyrophosphate | 4 |
| Glycerol | 50 |
| Magnesium oxide | 5 |
| Diatomaceous earth | 9 |
| Sodium fluoride | 2 |
| Example 6(d). | |
| Calcium sulfate | 50 |
| Trisodium phosphate | 3 |
| Glycerol | 2 |
| Mineral oil | 40 |
| Magnesium oxide | 5 |
| Example 6(e). | |
| Calcium sulfate | 60 |
| Tetrasodium pyrophosphate | 4 |
| Silicone oil | 34 |
| Zinc oxide | 1.5 |
| Zinc fluoride | 0.5 |
| Example 6(f). | |
| Calcium sulfate | 10 |
| Tetrasodium pyrophosphate | 0.5 |
| Oleyl alcohol | 55 |
| Magnesium oxide | 10 |
| Potassium zinc fluoride | 3 |
| Talc | 21.5 |

EXAMPLE VII

The following composition was prepared as a blend in the manner of the prior art.

| INGREDIENTS | WT. % |
|---|---|
| Sodium alginate | 11 |
| Diatomaceous earth | 60 |
| Tetrapotassium pyrophosphate | 1 |
| Dextrose | 5 |
| Diethylene glycol | 2 |
| Calcium sulfate | 14 |
| Potassium titanium fluoride | 2 |
| Magnesium oxide | 5 |
| Preservative | Trace |
| Flavor | Trace |

Promptly following preparation of the composition, a first portion thereof was mixed with a suitable amount of water and evaluated for set time which was 3 minutes. A second portion of the composition was stored for 6 months at 55% humidity and then evaluated for pre-mix shelf life, ease of mixing and set time. The stored composition had aggregated in the container, and when mixed with water was grainy and difficult to mix. The set time for the stored composition was 1.5 minutes. It is theorized that this shelf life deterioration is due to moisture absorption which allows the calcium sulfate to interact with a significant quantity of the tetrapotassium phyrophosphate.

EXAMPLE VIII

This example shows that if the alkali metal alginate component (Component A) is formulated with a metal oxide and a double metal salt, shelf life stability begins to deteriorate within a relatively short time period.

| COMPONENT A | PARTS BY WT. |
|---|---|
| Sodium alginate | 10 |
| Diatomaceous earth | 60 |
| Tetrasodium pyrophosphate | 0.3 |
| Magnesium oxide | 10 |
| Potassium titanium fluoride | 0.5 |
| Fructose | 3 |
| Glycerol | 7 |
| Water | 140 |
| Flavor | Trace |
| Color | Trace |
| Preservative | Trace |

4 volumes of Component A were mixed with 1 volume of Component B having the formulation set forth in Example I and the system was evaluated for ease of mixing, set time and compressive strength as follows:

| | WHEN FIRST PREPARED | 30 DAYS AFTER PREPARATION |
|---|---|---|
| Ease of mixing | Very easy | Very easy |
| Set time, minutes | 3 | 3 |
| Compressive Strength | 900g/Sq. in. | 600g/Sq. in. |

EXAMPLE IX

This example illustrates a two-component alginate formulation which, when blended, provides a relatively low viscosity, settable composition that is adapted to be applied with a syringe to a dental surface or other body part such as an ear for making an impression for use in constructing an appropriate form.

| COMPONENT A | Parts By wt. | COMPONENT B | Parts By Wt. |
|---|---|---|---|
| Water | 440.00 | Almond oil, sweet | 60 |
| Tetrapotassium pyrophosphate | 1.73 | Vaseline petroleum jelly | 12 |
| Potassium alginate | 30.00 | Polyglycol 15-200 (Dow) | 6 |
| Glycerol | 2.00 | Potassium fluoride | 15 |
| Silicone oil | 1.00 | Magnesium oxide | 15 |
| Polyacrylamide | 2.62 | Calcium sulfate | 45 |
| | | Tetrapotassium pyrophosphate | 1 |
| | | Alumina | 50 |
| | | Zinc oxide | 15 |
| | | Color | 9 |

U.S. Pat. No. 2,756,874 (Erickson et al, 1956) discloses a self-contained, two-component alginate impression system, wherein one component contains potassium alginate and tetrasodium pyrophosphate in an aqueous paste and the other component contains calcium sulfate in an aqueous paste. The patentees point out and emphasize that the reactant (calcium sulfate) and retarder (tetrasodium pyrophosphate) cannot be incorporated in the same aqueous composition. The invention described herein is distinguishable from the disclosure of U.S. Pat. No. 2,756,874 in that the divalent metal salt component contains both reactant (calcium sulfate) and retarder (tetrasodium phrophosphate) in a non-aqueous fluid plasticizer paste.

In view of the foregoing description and examples, it will become apparent to those of ordinary skill in the art that equivalent modifications thereof may be made without departing from the spirit and scope of this invention.

That which is claimed is:

1. A two-component system interactable to form an oral, settable, dental composition comprising:
   (i) Component A consisting essentially of an alkali metal alginate selected from the group consisting of sodium alginate, potassium alginate and mixtures thereof in an aqueous paste; and
   (ii) Component B consisting essentially of a slightly water soluble, divalent metal salt and a reaction rate retarder in a fluid plasticizer paste that is substantially free of unbound water, said Component B being so formulated that a pre-selected quantity thereof contains from about 0.5 to about 1.2 parts by weight of divalent metal salt per 1.0 part by weight of alkali metal alginate in Component A, said reaction rate retarder being present in an amount from about 0.02 to about 0.13 part by weight per 1.0 part by weight of said divalent metal salt, and said fluid plasticizer being present in an amount from about 0.75 to about 2 parts by weight per 1.0 part by weight of said divalent metal salt, wherein:
   said divalent metal salt is a member selected from the group consisting of calcium sulfate, ferrous sulfate, zinc sulfate, divalent metal salt of fatty acid and mixtures thereof,
   said reaction rate retarder is a member selected from the group consisting of phosphate, pyrophosphate, citrate and silicate salts of sodium, potassium and mixtures thereof, and
   said fluid plasticizer is a member selected from the group consisting of glycerol, propylene glycol, polyether glycol, oleyl alcohol, silicone oil, mineral oil, vegetable oil and mixtures thereof.

2. The two-component system of claim 1 wherein Component B is so formulated that a pre-selected quantity thereof contains from about 0.75 to about 1.0 part by weight of divalent metal salt per 1.0 part by weight of alkali metal alginate in Component A.

3. The two-component system of claim 1 wherein the reaction rate retarder is present in Component B in an amount from about 0.04 to about 0.08 part by weight per 1.0 part by weight of said divalent metal salt.

4. The two-component system of claim 1 wherein the fluid plasticizer is present in Component B in an amount from about 0.9 to about 1.5 parts by weight per 1.0 part by weight of divalent metal salt.

5. The two-component system of claim 1 wherein the divalent metal salt of fatty acid is selected from the group consisting of calcium oleate, zinc laurate, and ferrous stearate.

6. The two-component system of claim 1 wherein the divalent metal salt is calcium sulfate.

7. The two-component system of claim 1 wherein the fluid plasticizer is vegetable oil.

8. The two-component system of claim 1 wherein the fluid plasticizer is a mixture of vegetable oil and polyether glycol.

9. The two-component system of claim 1 wherein the fluid plasticizer is glycerol.

10. The two-component system of claim 1 wherein Component B includes from about 0.02 to about 1.0 part by weight of metal oxide selected from the group consisting of zinc oxide, magnesium oxide and mixtures thereof per 1.0 part by weight of divalent metal salt.

11. The two-component system of claim 1 wherein Component A includes a filler in an amount from about 3 to about 10 parts by weight per 1.0 part by weight of alkali metal alginate, and water in an amount from about 13 to about 25 parts by weight per 1.0 part by weight of alkali metal alginate.

12. The two-component system of claim 11 wherein Component A includes a reaction rate retarder selected from the group consisting of phosphate, pyrophosphate, citrate and silicate salts of sodium, potassium and mixtures thereof in an amount from about 0.02 to about 0.08 part by weight per 1.0 part by weight of alkali metal alginate.

13. The two-component system of claim 12 wherein Component A includes a humectant in an amount from about 0.1 to about 1.0 part by weight per 1.0 part by weight of alkali metal alginate.

14. A method for preparing an oral, settable, dental composition which comprises interacting:
   (i) Component A consisting essentially of an alkali metal alginate selected from the group consisting of sodium alginate, potassium alginate and mixtures thereof in an aqueous paste; and
   (ii) Component B consisting essentially of a slightly water soluble, divalent metal salt and a reaction rate retarder in a fluid plasticizer paste that is substantially free of bound water, said divalent metal salt being present in an amount from about 0.5 to about 1.2 parts by weight per 1.0 part by weight of alkali metal alginate, said reaction rate retarder being present in an amount of about 0.02 to about 0.13 part by weight per 1.0 part by weight of said divalent metal salt, and said fluid plasticizer being present in an amount from about 0.75 to about 2 parts by weight per 1.0 part by weight of said divalent metal salt, wherein:

said divalent metal salt is a member selected from the group consisting of calcium sulfate, ferrous sulfate, zinc sulfate, divalent metal salt of fatty acid and mixtures thereof, said reaction rate retarder is a member selected from the group consisting of phosphate, pyrophosphate, citrate and silicate salts of sodium, potassium and mixtures thereof, and said fluid plasticizer is a member selected from the group consisting of glycerol, propylene glycol, polyether glycol, oleyl alcohol, silicone oil, mineral oil, vegetable oil and mixtures thereof.

15. The method of claim 14 wherein the divalent metal salt of fatty acid is selected from the group consisting of calcium oleate, zinc laurate, and ferrous stearate.

16. The method of claim 14 wherein the divalent metal salt is calcium sulfate.

17. The method of claim 14 wherein the fluid plasticizer is vegetable oil.

18. The method of claim 14 wherein the fluid plasticizer is a mixture of vegetable oil and polyether glycol.

19. The method of claim 14 wherein the fluid plasticizer is glycerol.

20. The method of claim 14 wherein Component B includes a metal oxide selected from the group consisting of zinz oxide, magnesium oxide and mixtures thereof in an amount from about 0.02 to about 1.0 part by weight per 1.0 part by weight of divalent metal salt.

21. The method of claim 14 wherein Component A includes a filler in an amount from about 3 to about 10 parts by weight per 1.0 part by weight of alkali metal alginate, and water in an amount from about 13 to about 25 parts by weight per 1.0 part by weight of alkali metal alginate.

22. The method of claim 21 wherein Component A includes a reaction rate retarder selected from the group consisting of phosphate, pyrophosphate, citrate, and silicate salts of sodium, potassium and mixtures thereof, in an amount from about 0.02 to about 0.08 part by weight per 1.0 part by weight of alkali metal alginate.

23. The method of claim 22 wherein Component A includes a humectant in an amount from about 0.1 to about 1.0 part by weight per 1.0 part by weight of alkali metal alginate.

24. A solid, coherent, dental composition prepared by interacting:
(i) Component A consisting essentially of an alkali metal alginate selected from the group consisting of sodium alginate, potassium alginate and mixtures thereof in an aqueous paste; and
(ii) Component B consisting essentially of a slightly water soluble, divalent metal salt and a reaction rate retarder in a fluid plasticizer paste that is substantially free of bound water, said divalent metal salt being present in an amount from about 0.5 to about 1.2 parts by weight per 1.0 part by weight of alkali metal alginate, said reaction rate retarder being present in an amount from about 0.02 to about 0.13 part by weight per 1.0 part by weight of said divalent metal salt and said fluid plasticizer being present in an amount from about 0.75 to about 2 parts by weight per 1.0 part by weight of said divalent metal salt, wherein:

said divalent metal salt is a member selected from the group consisting of calcium sulfate, ferrous sulphate, zinc sulfate, divalent metal salt of fatty acid and mixtures thereof, said reaction rate retarder is a member selected from the group consisting of phosphate, pyrophosphate, citrate and silicate salts of sodium, potassium and mixtures thereof, and said fluid plasticizer is a member selected from the group consisting of glycerol, propylene glycol, polyether glycol, oleyl alcohol, silicone oil, mineral oil, vegetable oil and mixtures thereof.

* * * * *